(12) United States Patent
Sutton et al.

(10) Patent No.: US 10,835,731 B2
(45) Date of Patent: *Nov. 17, 2020

(54) HEMOSTASIS SEALING DEVICE

(71) Applicant: NorMedix, Inc., Eden Prairie, MN (US)

(72) Inventors: Gregg Stuart Sutton, Plymouth, MN (US); Eric Joseph Dille, Eden Prairie, MN (US)

(73) Assignee: NorMedix, Inc., Eden Prairie, MN (US)

( * ) Notice: Subject to any disclaimer, the term of this patent is extended or adjusted under 35 U.S.C. 154(b) by 439 days.

This patent is subject to a terminal disclaimer.

(21) Appl. No.: 15/348,772

(22) Filed: Nov. 10, 2016

(65) Prior Publication Data

US 2017/0087349 A1 Mar. 30, 2017

Related U.S. Application Data

(63) Continuation of application No. 13/407,569, filed on Feb. 28, 2012, now Pat. No. 9,522,266.
(Continued)

(51) Int. Cl.
*A61M 39/06* (2006.01)
*A61B 17/34* (2006.01)
(Continued)

(52) U.S. Cl.
CPC ..... *A61M 39/0613* (2013.01); *A61B 17/0218* (2013.01); *A61B 17/3423* (2013.01);
(Continued)

(58) Field of Classification Search
CPC ............ A61B 17/3423; A61B 17/3462; A61B 17/3498; A61B 2017/3464;
(Continued)

(56) References Cited

U.S. PATENT DOCUMENTS 4,960,412 A * 10/1990 Fink .................. A61M 39/0606
604/167.04
5,092,857 A 3/1992 Fleischhacker
(Continued)

FOREIGN PATENT DOCUMENTS

WO WO-2012118852 A2 9/2012

OTHER PUBLICATIONS

US 5,520,663 A, 05/1996, Patterson et al. (withdrawn)
(Continued)

*Primary Examiner* — Robert A Lynch
(74) *Attorney, Agent, or Firm* — Schwegman Lundberg & Woessner, P.A.

(57) ABSTRACT

The present technology relates to a hemostasis sealing device having a device enclosure with a first seal portion for a medical device and a second seal portion for guide wire sealing. The device enclosure can be generally configured for compressive communication with a housing. The second seal portion can define a split that is in compressive communication with structural elements of the hemostasis sealing device, which can simultaneously provide sealing functionality and allow passage of relatively large-bore devices.

20 Claims, 6 Drawing Sheets

Related U.S. Application Data

(60) Provisional application No. 61/447,496, filed on Feb. 28, 2011.

(51) Int. Cl.
*A61B 17/02* (2006.01)
*A61M 25/06* (2006.01)
*A61M 25/09* (2006.01)

(52) U.S. Cl.
CPC ...... *A61B 17/3462* (2013.01); *A61B 17/3498* (2013.01); *A61M 25/06* (2013.01); *A61M 25/09041* (2013.01); *A61M 39/06* (2013.01); *A61B 2017/3464* (2013.01)

(58) Field of Classification Search
CPC .......... A61B 2017/3466; A61M 39/06; A61M 39/0606; A61M 39/0613; A61M 2039/062; A61M 2039/0626; A61M 2039/0633; A61M 2039/064; A61M 2039/0646; A61M 2039/066; A61M 2039/0673; A61M 2039/0686
See application file for complete search history.

(56) References Cited

U.S. PATENT DOCUMENTS

| | | | |
|---|---|---|---|
| 5,114,408 A | 5/1992 | Fleischhaker et al. | |
| 5,125,903 A | 6/1992 | McLaughlin et al. | |
| 5,195,980 A | 3/1993 | Catlin | |
| 5,207,649 A | 5/1993 | Aruny | |
| 5,269,764 A | 12/1993 | Vetter et al. | |
| 5,300,033 A | 4/1994 | Miller | |
| 5,304,156 A | 4/1994 | Sylvanowicz et al. | |
| 5,312,362 A * | 5/1994 | Pfolsgraf ........... A61B 17/3462 137/849 |
| 5,324,271 A | 6/1994 | Abiuso et al. | |
| 5,336,192 A | 8/1994 | Palestrant | |
| 5,443,452 A * | 8/1995 | Hart ................... A61B 17/3498 137/849 |
| 5,453,095 A | 9/1995 | Davila | |
| 5,456,284 A * | 10/1995 | Ryan ................. A61B 1/00137 137/522 |
| 5,507,732 A | 4/1996 | Mcclure et al. | |
| 5,520,655 A | 5/1996 | Davila et al. | |
| 5,549,576 A | 8/1996 | Patterson et al. | |
| 5,603,702 A | 2/1997 | Smith et al. | |
| 5,613,956 A | 3/1997 | Patterson et al. | |
| 5,643,227 A | 7/1997 | Stevens | |
| 5,702,370 A | 12/1997 | Sylvanowicz et al. | |
| 5,858,007 A | 1/1999 | Fagan et al. | |
| 5,935,112 A | 8/1999 | Stevens et al. | |
| 6,024,729 A | 2/2000 | Dehdashtian et al. | |
| 6,053,861 A | 4/2000 | Grossi | |
| 6,086,570 A | 7/2000 | Aboul-Hosn et al. | |
| 6,142,981 A | 11/2000 | Heck et al. | |
| 6,551,283 B1 | 4/2003 | Guo et al. | |
| 6,632,200 B2 | 10/2003 | Guo et al. | |
| 6,702,255 B2 | 3/2004 | Dehdashtian | |
| 6,712,791 B2 | 3/2004 | Lui et al. | |
| 7,081,106 B1 | 7/2006 | Guo et al. | |
| 7,101,353 B2 | 9/2006 | Lui et al. | |
| 7,241,276 B2 | 7/2007 | Argentine et al. | |
| 7,582,070 B2 | 9/2009 | Goode et al. | |
| 7,628,774 B2 | 12/2009 | Fangrow, Jr. | |
| 7,731,694 B2 | 6/2010 | Becker | |
| 7,901,379 B2 | 3/2011 | Argentine et al. | |
| 7,938,806 B2 * | 5/2011 | Fisher ............... A61M 25/0668 604/167.04 |
| 7,976,503 B2 | 7/2011 | Khan | |
| 8,016,791 B2 | 9/2011 | Sugiki et al. | |
| 8,048,033 B2 | 11/2011 | Becker | |
| 8,096,976 B2 | 1/2012 | Sugiki et al. | |
| 8,137,321 B2 | 3/2012 | Argentine | |
| 8,177,760 B2 | 5/2012 | Rome et al. | |
| 8,246,585 B2 | 8/2012 | Schennib | |
| 8,273,059 B2 | 9/2012 | Nardeo et al. | |
| 8,444,628 B2 | 5/2013 | Fangrow, Jr. | |
| 8,523,822 B2 | 9/2013 | Nardeo et al. | |
| 8,790,309 B2 | 7/2014 | Goode et al. | |
| 8,870,850 B2 | 10/2014 | Fangrow, Jr. | |
| 9,005,172 B2 | 4/2015 | Chung | |
| 9,522,266 B2 | 12/2016 | Sutton et al. | |
| 2003/0050604 A1 * | 3/2003 | Lui ................... A61M 25/0668 604/167.06 |
| 2004/0260243 A1 | 12/2004 | Rickerd | |
| 2005/0020981 A1 | 1/2005 | Kurth | |
| 2009/0012476 A1 | 1/2009 | Catlin | |
| 2009/0259175 A1 | 10/2009 | Nordgren | |
| 2010/0241078 A1 | 9/2010 | Barnes | |
| 2010/0292638 A1 | 11/2010 | Becker et al. | |
| 2010/0331453 A1 | 12/2010 | Fisher et al. | |
| 2012/0221024 A1 | 8/2012 | Sutton et al. | |
| 2012/0245527 A1 | 9/2012 | Stephens et al. | |
| 2014/0343512 A1 | 11/2014 | Fischer et al. | |
| 2015/0157843 A1 | 6/2015 | Pepin et al. | |

OTHER PUBLICATIONS

"U.S. Appl. No. 13/407,568, Response filed Jul. 1, 2016 to Non Final Office Action dated Mar. 1, 2016", 14 pgs.

"U.S. Appl. No. 13/407,569, Final Office Action dated May 21, 2014", 14 pgs.

"U.S. Appl. No. 13/407,569, Final Office Action dated Aug. 10, 2015", 19 pgs.

"U.S. Appl. No. 13/407,569, Non Final Office Action dated Mar. 1, 2016", 19 pgs.

"U.S. Appl. No. 13/407,569, Non Final Office Action dated Jul. 31, 2013", 8 pgs.

"U.S. Appl. No. 13/407,569, Non Final Office Action dated Nov. 13, 2014", 15 pgs.

"U.S. Appl. No. 13/407,569, Notice of Allowance dated Aug. 9, 2016", Examiner Interview Summary dated Aug. 9, 2016 included, 10 pgs.

"U.S. Appl. No. 13/407,569, PTO Response to Rule 312 Communication dated Nov. 17, 2016", 2 pgs.

"U.S. Appl. No. 13/407,569, Response filed Jan. 31, 2014 to Non Final Office Action dated Jul. 31, 2013", 10 pgs.

"U.S. Appl. No. 13/407,569, Response filed Feb. 10, 2016 to Final Office Action dated Aug. 10, 2015", 17 pgs.

"U.S. Appl. No. 13/407,569, Response filed May 13, 2015 to Non Final Office Action dated Nov. 13, 2014", 10 pgs.

"U.S. Appl. No. 13/407,569, Response filed Oct. 21, 2014 to Final Office Action dated May 21, 2014", 17 pgs.

"Application Serial No. PCT/US2012/027012, International Preliminary Report on Patentability dated Sep. 12, 2013", 6 pgs.

"International Application Serial No. PCT/US2007/072357, International Search Report dated Aug. 12, 2008", 2 pgs.

"International Application Serial No. PCT/US2007/072357, Written Opinion dated Aug. 12, 2008", 6 pgs.

* cited by examiner

HEMOSTASIS SEALING DEVICE

This application is a continuation of U.S. application Ser. No. 13/407,569, filed Feb. 28, 2012, which claims the benefit of U.S. Provisional Application No. 61/447,496, filed Feb. 28, 2011, the contents of which are herein incorporated by reference.

FIELD OF THE INVENTION

The present invention pertains to a medical device for providing a leak-resistant seal for use in a vascular access device.

BACKGROUND OF THE INVENTION

When interventional catheter devices are inserted into the vascular system, the physician usually starts with a needle stick, followed by dilating the artery in order to insert an introducer sheath device that is left in place for the duration of the procedure. This introducer sheath acts as the main conduit for entry of subsequent therapeutic or diagnostic devices. In most instances, these introducer sheaths contain a hemostatic component that restricts back-flow of blood from the artery. These hemostasis seals are generally passive and provide sealing around the catheter devices and guide wires that are used during the procedure.

Current devices and prior art for hemostasis seals have limited performance when they are made for large size devices. This is due to the extreme size difference between the large catheter device and the much smaller guide wire used in these procedures. When larger catheter devices are used (such as 14-20 Fr), it can be difficult to seal on both this large diameter and on the guide wires used in these types of procedures, which are generally 0.035" in diameter. Current seals tend to leak when only the guide wire is in place or when nothing is in place, especially after large diameter devices have passage through the sealing device and have stretched or damaged the seal in the process.

It is the objective of this invention to provide a hemostasis sealing device for large bore interventional devices that provides a leak-proof or leak resistant blood seal on both guide wire passage as well as device passage through the seal.

SUMMARY OF THE INVENTION

The present invention is directed to a device for vascular access, in particular a hemostasis sealing device that has a first seal for large device sealing and a second seal for guide wire sealing. The first seal is often formed using a hole seal or a wring seal, while the second seal is often formed using a split, septum seal. The split, septum seal can optionally be held by compression with a mating housing. In some implementations the second, guide wire seal comprises an extended barrel portion to inhibit seal inversion or misalignment. The hemostasis sealing device can include support ring configured for compressive interface with a housing. The second seal may comprise a single axial split approximately forty five degrees offset from the support ribs.

The above summary of the present invention is not intended to describe each disclosed embodiment of the present invention. This is the purpose of the detailed description and claims that follows.

BRIEF DESCRIPTION OF THE DRAWINGS

The invention may be more completely understood in consideration of the following detailed description of various embodiments of the invention in connection with the accompanying drawings, in which.

These drawings are to be considered general representations of the invention, and it will be appreciated that they are not drawn to encompass all embodiments of the invention, nor are they always drawn to scale. While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION

The present invention is directed to a device for vascular access, in particular a hemostasis sealing device that has a first seal portion for device sealing and a second seal portion for guide wire sealing. As a vascular access device is passed over a guide wire during a procedure, the device passes through a first seal portion which stretches and seals around the medical device. While the second seal portion is generally configured for guide wire sealing, a split defined by the second seal portion allows passage of relatively large bore devices.

The first seal portion can be a hole seal or a wring seal, while the second seal portion can be a split, septum seal. The hemostasis sealing device generally has structural elements that are configured to structurally support the second seal portion for sealing. In a variety of embodiments, the second seal portion is held in compression by a housing that compressively interfaces with the hemostasis sealing device. In such an embodiment, support ribs can be in compressive communication with the second seal portion. The split of the second seal portion can be an axial split offset from the support ribs. In some implementations a barrel extends from the second seal portion to inhibit seal inversion or misalignment.

Figure 1:
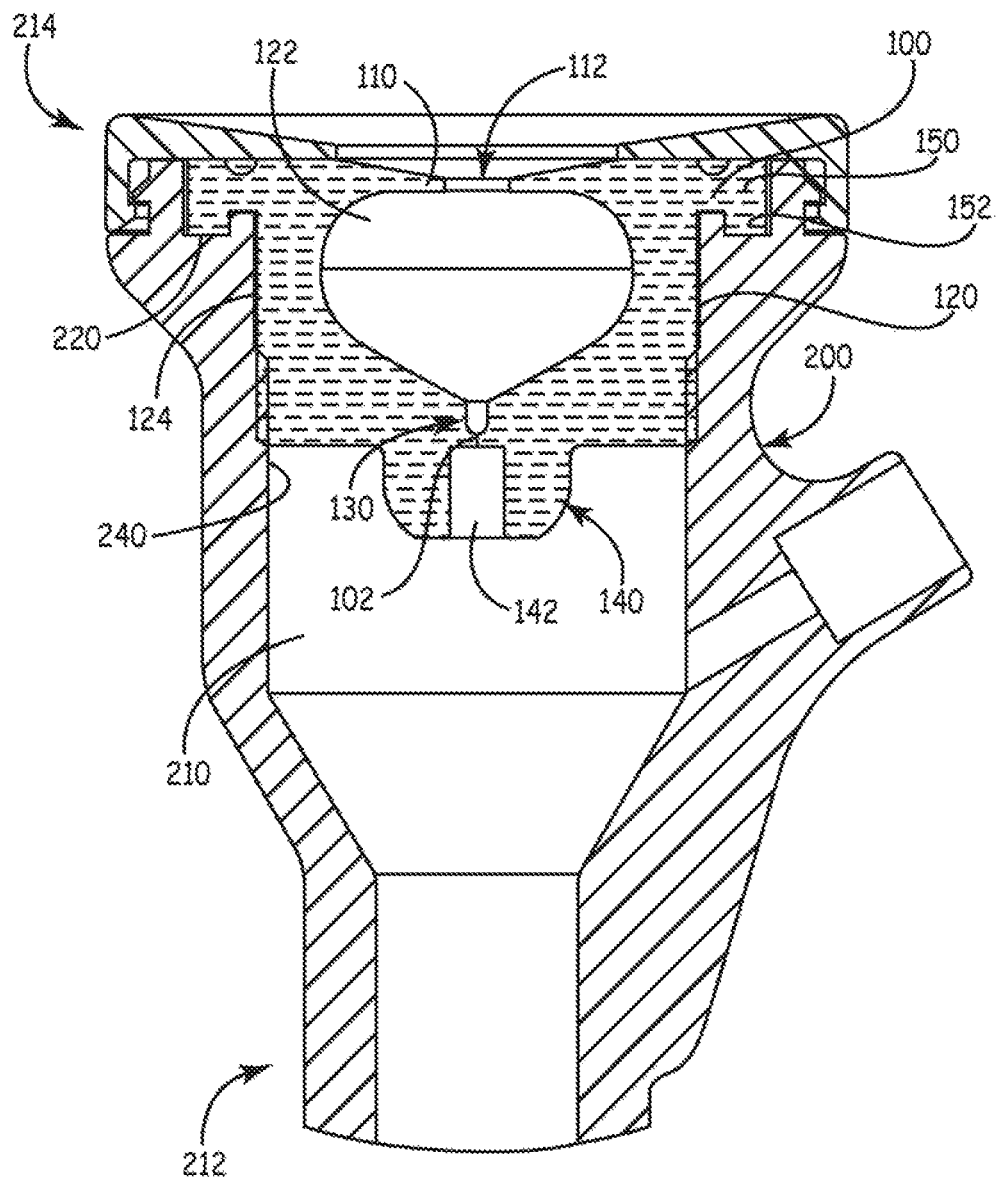
FIG. 1 is a cross-sectional view of an example hemostasis sealing device consistent with the technology disclosed herein.

An example embodiment of such a hemostasis sealing device is shown in FIG. 1. The hemostasis sealing device 100 is disposed in a housing 200 and has a device enclosure 120 in communication with a first seal portion 110 on a support ring 150, a second seal portion 130, and a barrel 140. The housing 200 is generally an introducer sheath, but could be another device that is generally rigid and defines a passageway 210 extending from the distal end 214 of the housing 200 to a proximal end 212 of the housing 200.

The hemostasis sealing device 100 is generally configured to provide a fluid seal for vascular access devices and simultaneously allowing translation or movement of a guide wire while providing a fluid seal there-around. The hemostasis sealing device 100 can be constructed of a variety of materials such as, for example, silicone rubber in the range of 10-60 Shore A durometer. In another example, the hemostasis sealing device 100 can be constructed so as to contain nitinol elements. Those having skill in the art will recognize that the hemostasis sealing device 100 can be constructed of various thermoplastic elastomers, and combinations thereof, available and known.

The hemostasis sealing device 100 is configured to be received by the distal end 214 of the housing 200. In at least one embodiment the hemostasis sealing device 100 is in compression upon being received by the housing 200. In one embodiment the compression of the hemostasis sealing device 100 is in the range of 0-5% of the diameter of the seal body. This compression allows the sealing device 100 to be firmly held within the housing 200.

The hemostasis sealing device 100 has a device enclosure 120 defining a device cavity 122 and, as mentioned above, has the first seal portion 110 and the second seal portion 130. The first seal portion 110 is generally configured to provide a seal for a medical device passing into the device cavity 122, such as a vascular access device, and the second seal portion 130 is generally configured to provide a seal for a guide wire. The device cavity 122 is generally sized to receive at least a portion of the medical device.

In this particular embodiment, the support ring 150 has a radial flange 152 and is received by a ring receptacle 220 defined by the housing 200. In some embodiments, the support ring 150 will be relatively rigid compared to some portions of the hemostasis sealing device 100. An outer annular surface 124 of the hemostasis sealing device 100 is received by the distal end 214 of the passageway 210 of the housing 200. In at least one embodiment, the housing 200 exerts compressive force on the outer annular surface 124 of the hemostasis sealing device 100.

The first seal portion 110 is generally elastomeric and defines a first seal opening 112 that is sized to seal around the medical device passing there-through. In one embodiment, the first seal portion 110 is a sealing hole. In another embodiment, the first seal portion 110 is a sealing ring. Typically the first seal opening 112 defined by the first seal portion 110 is sized in the range of 0.2-0.4 times the diameter of the largest device size that is to be inserted through a given seal. For instance, for a 20 Fr device (0.260 in. diameter), the first seal opening 112 size would be in the range of 0.052-0.104 in. in diameter.

The second seal portion 130 is similarly elastomeric to the first seal portion 110 and defines a split 102 there-through. The split 102 will generally be axial relative to the second seal portion 130, and can also be axial relative to the hemostasis sealing device 100 itself. In a variety of embodiments, the second seal portion 130 has a thickness in the range of 0.005-0.020 inches and a diameter in the range of 0.9-1.3 times the diameter of the guide wire to be used. Given the size differential between the first seal portion 110 and the second seal portion 130, in the current embodiment, the cross section of the device cavity 122 generally tapers towards the second seal portion 130. Those having skill in the art will recognize that the second seal portion 130 can be consistent with a split septum seal. In a variety of embodiments, structural elements of the hemostasis sealing device 100 are configured to provide structural support to the second seal portion 130. As one example, the compression fit between the hemostasis sealing device 100 and the housing 200 compresses the second seal portion 130 at the split 102 to be in sealing engagement with a guide wire.

A barrel 140 of the hemostasis sealing device 100 generally extends from the second seal portion 130. The barrel 140 is generally annular and coaxial with the second seal portion 130. The barrel 140 defines a barrel opening 142, a substantial portion of which is cylindrical in shape. The barrel 140 is generally configured to provide structural support to the second seal portion 130. In at least one embodiment, the barrel 140 prevents the split 102 of the second seal portion 130 from becoming misaligned and/or inverted on itself, wherein misalignment and inversion can inhibit complete sealing.

Figure 2:
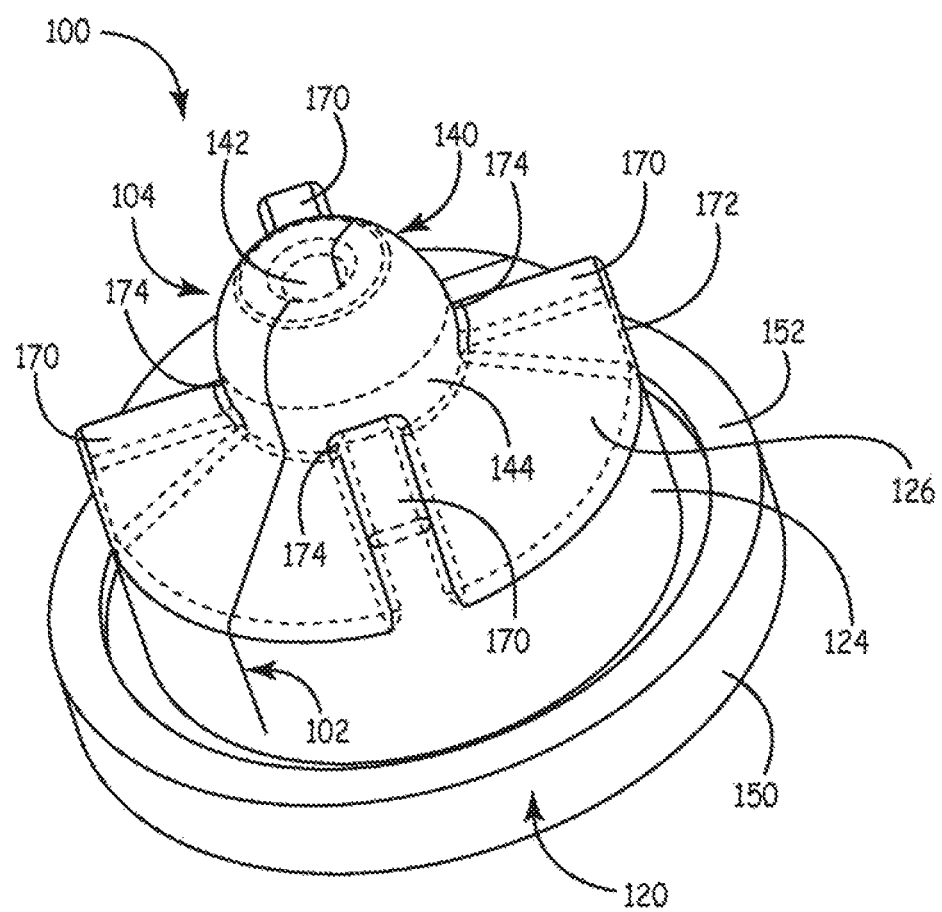
FIG. 2 is a perspective view of an example hemostasis sealing device consistent with the technology disclosed herein.

FIG. 2 depicts a perspective view of the hemostasis sealing device 100 of FIG. 1. From this view the overall configuration of the split is more clearly visible and the outer configuration of the device enclosure 120 and the support ribs 170 are visible.

The split 102 is generally defined from the proximal end 104 of the hemostasis sealing device 100, through the barrel 140 and the device enclosure 120, and extending towards the support ring 150. In a variety of embodiments the split 102 does not extend through the support ring 150 or the first seal portion 110. In a variety of implementations, it can be desirable for the hemostasis sealing device 100 to allow passage of large-bore devices, and the split 102 defined by the hemostasis sealing device 100 can accommodate such a use.

A tapered portion 126 of the device enclosure 120 extends between the outer annular portion 124 of the device enclosure 120 and the barrel 140. The tapered portion 126 can generally correspond with the tapered shape of the device cavity 122 and can extend adjacent to the second seal portion 130 (See FIG. 1). In the current embodiment the tapered portion 126, the annular surface 124, and the barrel 140 are a single cohesive unit. In some embodiments the annular surface 124, the barrel 140, and the tapered portion 126 can be an assembly of multiple components.

In a variety of implementations the hemostasis sealing device 100 includes two or more support ribs 170 along the tapered portion 124 of the device enclosure 120 in compressive communication with at least a portion of the split 102. As depicted in FIG. 2, the current embodiment has four support ribs 170. The support ribs 170 are generally configured to provide structural support to the hemostasis sealing device 100 when the hemostasis sealing device 100 is installed in a housing, such as the housing depicted in FIG. 1. The support ribs 170 can provide structural support to the hemostasis sealing device 100 particularly along the split 102 to ensure sealing of the second seal portion 130 (visible in FIG. 1) despite insertion of a medical device in the device enclosure 120.

In the current embodiment, an outer end surface 172 of each support rib 170 is coplanar with the outer annular surface 124 of the device enclosure 120. As such, the outer annular surface 124 of the device enclosure 120, the outer end surface 172 of each support rib 170 is configured for compressive interfacing with the inner annular surface 240 of the housing 200 (See FIG. 1). An inner end 174 of each support rib 170 contacts the outer surface 144 of the barrel 140, which can be adjacent to the second seal portion 130 (See FIG. 1). As such, despite expansion forces from the device cavity 122 and the first seal opening 122 (See FIG. 1) on the hemostasis sealing device 100 upon medical device insertion, reactive compressive forces by the housing 200 are exerted, in part, on the support ribs 170 and transferred to the barrel 140 and, therefore, around the second seal portion 130 of the hemostasis sealing device 100. Such compressive forces can prevent separation of the hemostasis sealing device 100 at least around the second seal portion 130.

It can be desirable to stagger the split 102 defined by the hemostasis sealing device 100 relative to the support ribs 170 such that relatively symmetrical compressive forces are applied about the second seal portion 130. In the current embodiment, the support ribs 170 are symmetrical relative to the split 102. The split 102 is offset from the support ribs 170 by about 45 degrees. Other configurations of support ribs relative to a split defined by a hemostasis sealing device are also possible.

Figure 3:
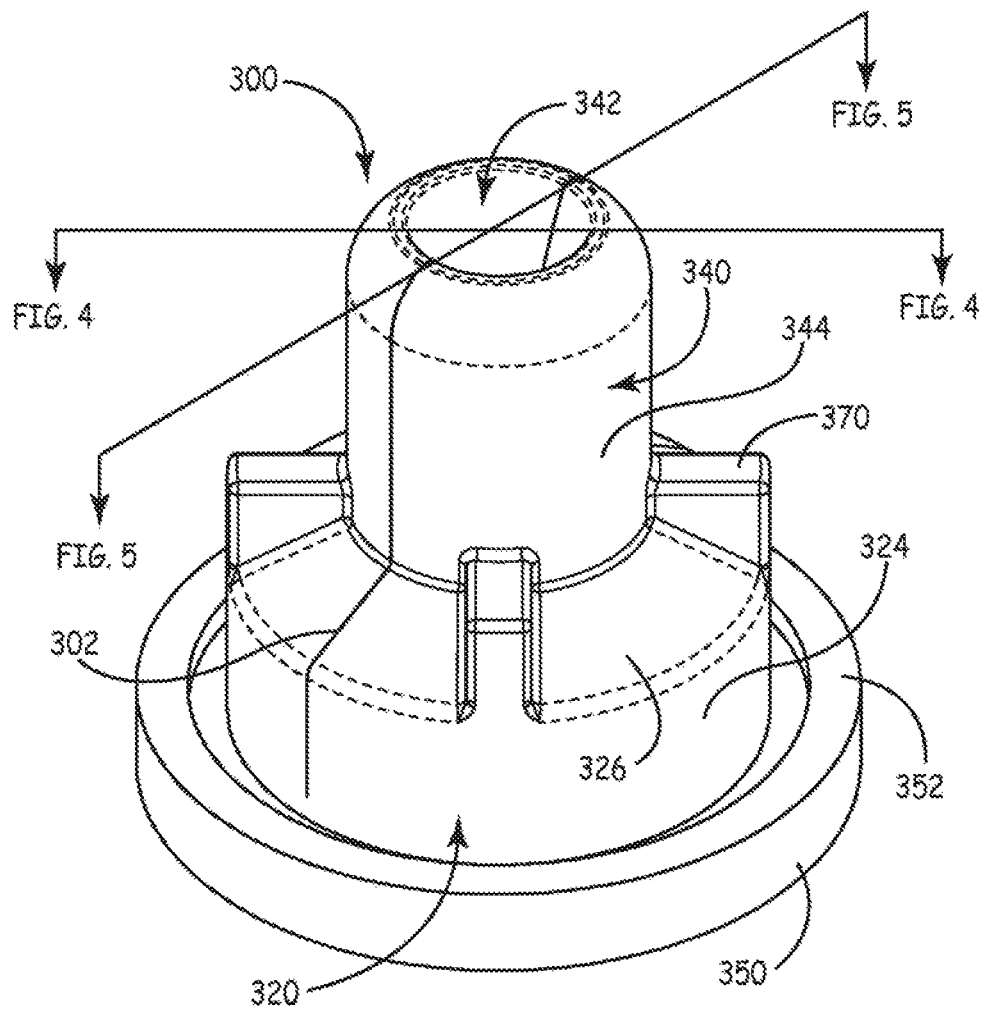
FIG. 3 is a perspective view of another example hemostasis sealing device consistent with the technology disclosed herein.

FIG. 3 is a perspective view of another embodiment of a hemostasis sealing device consistent with the technology disclosed herein. Similar to the hemostasis sealing device 100 depicted in FIG. 2, this hemostasis sealing device 300 has a device enclosure 320 with a first sealing portion and a second sealing portion (not visible in this view). The hemostasis sealing device 100 has a support ring 350 having a flange 352 coupled to the device enclosure 320 that has an outer annular surface 324 and a tapered portion 326. A barrel 340 defining an opening 342 is coupled to the tapered portion 326 and support ribs 370 extend along the tapered portion 326 from the outer annular surface 324 of the device enclosure 320 to the outer surface 344 of the barrel 340. A split 302 is defined by the hemostasis sealing device 300 from the proximal end 304 of the hemostasis sealing device 300 towards the support ring 350. The split 302 generally extends through the barrel 340 and the device enclosure 320.

Figure 4:
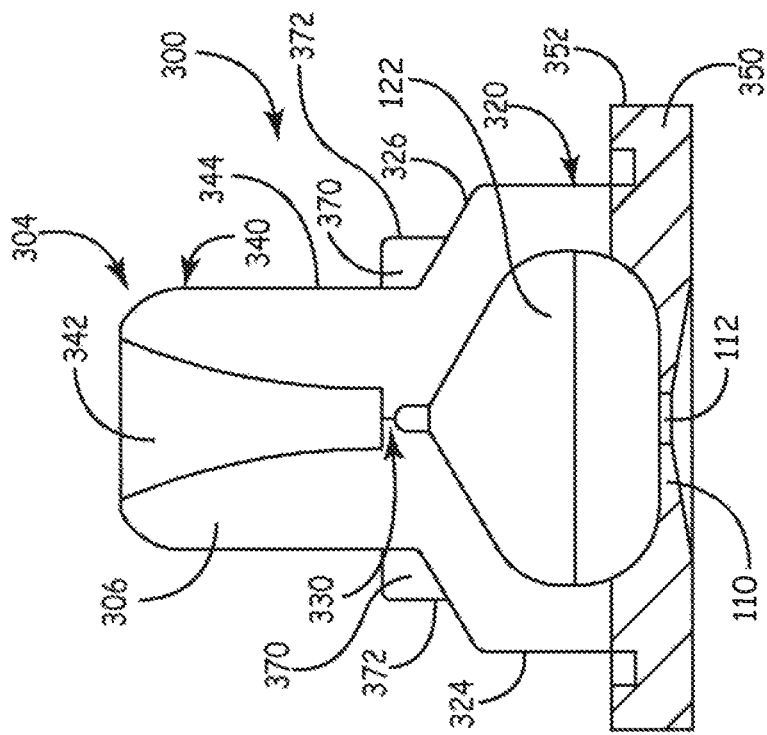
FIG. 4 is a cross-sectional view of the hemostasis sealing device of FIG. 3.
Figure 5:
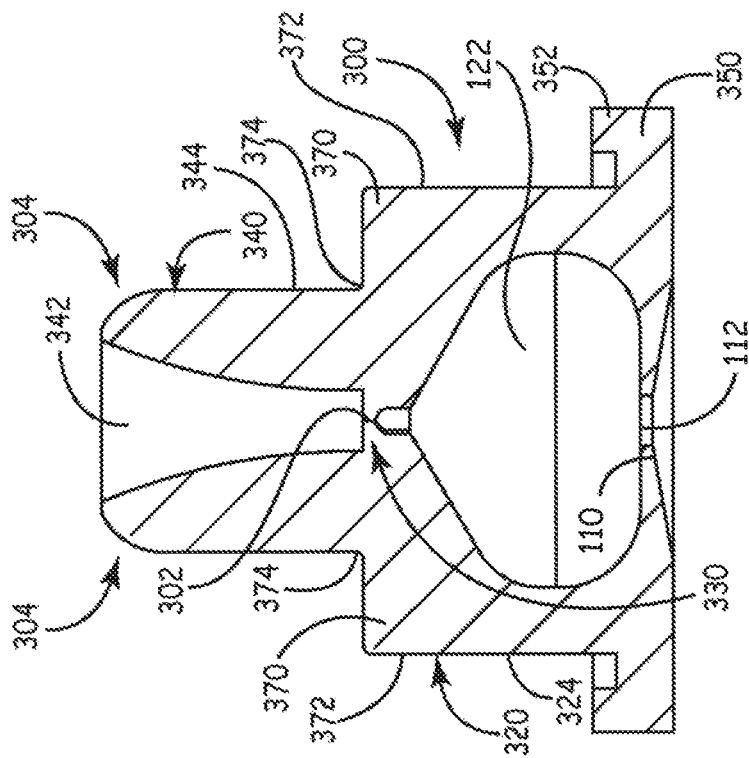
FIG. 5 is another cross-sectional view of the hemostasis sealing device of FIG. 3.

FIGS. 4 and 5 are cross-sectional views consistent with the hemostasis sealing device 300 of FIG. 3, as notated on FIG. 3. Specifically, FIG. 4 is a cross-sectional view of the hemostasis sealing device 300 through opposing support ribs 370. FIG. 5 is a cross-sectional view of the hemostasis sealing device 300 along the split 302 (See FIG. 3) revealing a split-defining surface 306 of the hemostasis sealing device 300 that is adjacent to the split 302 (FIG. 3). In FIG. 5 it is visible that the split-defining surface 306 and, therefore, the split 302 itself, extends from the proximal end 304 of the hemostasis sealing device 300, through the barrel 340 and the device enclosure 320 to the support ring 350. In the current embodiment the support ring 350 does not define any portion of the split 302.

Visible in FIG. 5, the annular surface 324 of the device enclosure 320 has a tapered portion 326 that couples to the barrel 340. Similar to the embodiment depicted in FIGS. 1-2, the support ribs 370 of the hemostasis sealing device 300 of FIGS. 3-5 are disposed along the tapered portion 326 and each have an outer end surface 372 that is substantially coplanar with the outer annular surface 324 of the device enclosure 320 and an inner end 374 adjacent to the second sealing portion 330. The inner end 374 of each rib 370 generally meets the outer surface 344 of the barrel 340. There are four support ribs 370 in this particular embodiment, which are staggered 45 degrees from the split 302.

In the embodiment depicted in FIGS. 4 and 5, the barrel opening 342 defined by the barrel 340 is at least partially tapered from the second seal portion 330 to the proximal end 304 of the hemostasis sealing device 300. Such a configuration can help prevent inversion of the second seal portion 330. Those having skill in the art will appreciate other configurations that could have similar advantages regarding the second seal portion 330.

Figure 6:
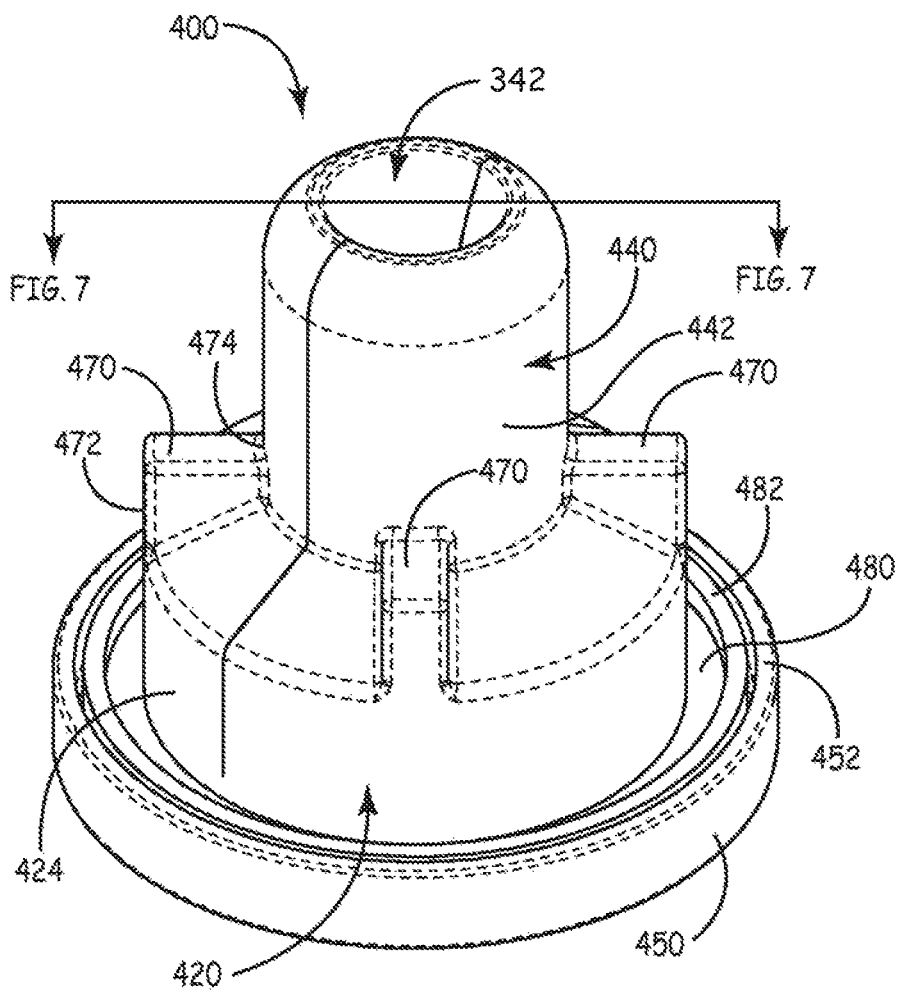
FIG. 6 is a perspective view of another example hemostasis sealing device consistent with the technology disclosed herein.
Figure 7:
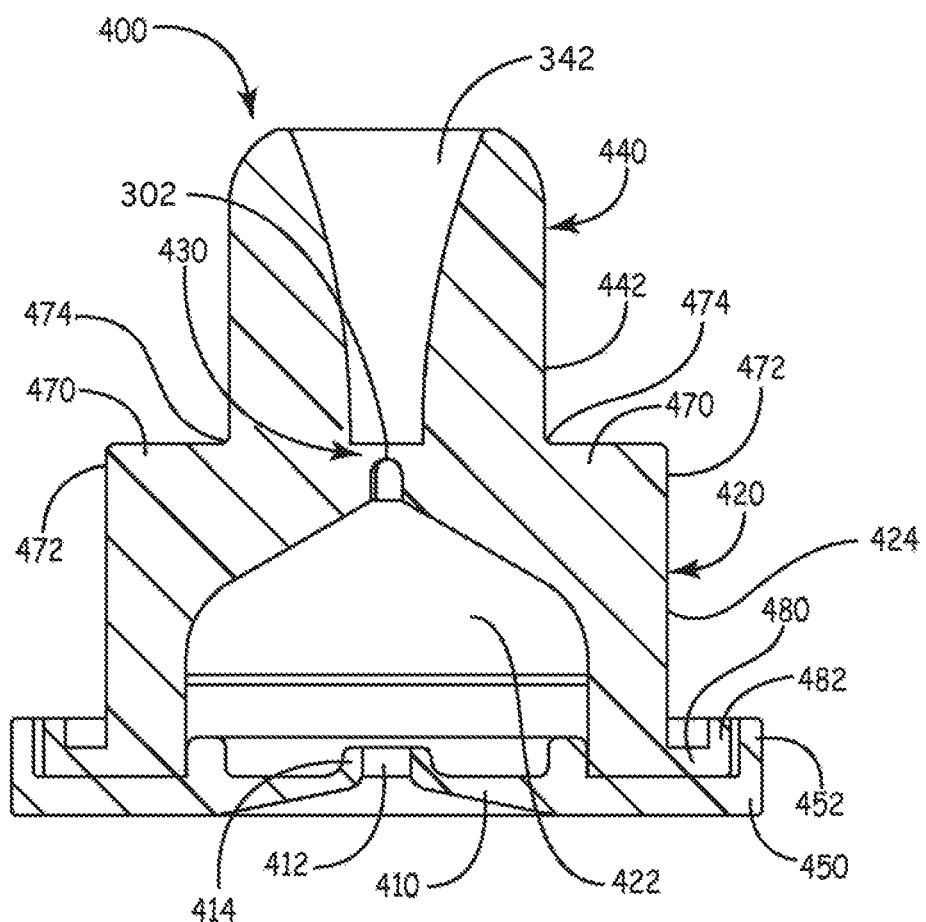
FIG. 7 is a cross-sectional view of the hemostasis sealing device of FIG. 6.

FIG. 6 is a perspective view of another embodiment of a hemostasis sealing device consistent with the technology disclosed herein. FIG. 7 is a cross-sectional view of the hemostasis sealing device 400 of FIG. 6. In this embodiment a first seal portion 410 and the second seal portion 430 are manufactured as separate components and are coupled to form a cohesive unit. The first seal portion 410 is defined by a support ring 450 having a flange 452 that is configured to engage a device enclosure 420 defining the second seal portion 430. A barrel 440 extends from the device enclosure 420 and is configured to provide structural support to the second seal portion 430. Support ribs 470 are additionally configured to provide structural support to the second seal portion 430. Each support rib 470 has an outer end surface 472 that is substantially coplanar with the outer annular surface 424 of the device enclosure 420 and an inner end 474 in compressive communication with the second seal portion 430. Each support rib 470 is configured to exert compressive force on the second seal portion 430, through the barrel outer surface 442, upon insertion of the hemostasis sealing device 400 in a housing such as an introducer sheath.

In the current embodiment the first seal portion 410 has a radial lip 414 extending into the device cavity 422 that at least partially defines a first seal opening 412. The radial lip 414 is generally configured to contribute to device sealing around a medical device.

The support ring 450 can be coupled to the device enclosure 420 through a variety of ways that will be known in the art. In one embodiment an adhesive is disposed between the support ring 450 and the device enclosure 420 to couple the components. In another embodiment the support ring flange 452 threadably engages a mating structure 480 defined by the device enclosure 420. The mating structure 480 can include a mating flange 482 that is configured to be concentric to the flange 452 of the support ring 450. The mating flange 482 can define a threaded surface that is configured to be received by the support ring flange 452. In some embodiments the support ring 450 is configured to be permanently fixed to the device enclosure 460. In other embodiments the support ring 450 is configured to be removably fixed to the device enclosure 460. Other configurations will be appreciated by those having skill in the art.

The above specification provides a complete description of the present invention. Since many embodiments of the invention can be made without departing from the spirit and scope of the invention, the invention resides in the claims hereinafter appended.

We claim:

1. A hemostasis sealing device configured for reception in a housing, the device comprising:
   a first seal portion having a first seal opening extending through the first seal portion, the first seal portion is configured for device sealing; and
   a second seal portion coupled with the first seal portion, the second seal portion is configured for guidewire sealing, the second seal portion includes:
   a second seal opening extending through the second seal portion;
   a barrel having a barrel opening surrounded by an inner perimeter of the barrel, wherein the inner perimeter of the barrel is spaced from the second seal opening within the barrel opening;
   one or more support ribs extending from an inner end proximate to an outer perimeter of the barrel to an outer end surface configured for compressive engagement with a housing inner surface of the housing; and
   wherein the one or more support ribs are configured to transmit compressive forces to the barrel, and the barrel is configured to transmit the compressive forces to the second seal portion within the barrel opening from the compressive engagement between the outer end surface and the housing inner surface.

2. The device of claim 1, wherein the first seal portion is separate from the second seal portion.

3. The device of claim 1, wherein the outer end surface of the support ribs is coplanar with an outer surface of a device enclosure of the hemostasis sealing device.

4. The device of claim 1, wherein the second seal opening includes a split extending from a distal portion of the second seal portion toward a proximal portion of the second seal portion.

5. The device of claim 4, wherein the split is offset from the one or more support ribs.

6. The device of claim 1 comprising a device enclosure including one or more of the first and second seal portions, the device enclosure includes a device cavity interposed between the first seal opening and the second seal opening.

7. The device of claim 1, wherein the barrel extends from a distal end of the second seal portion.

8. The device of claim 7, wherein the barrel opening is aligned with the second seal opening, and a barrel wall between the inner and outer perimeters of the barrel tapers from near the second seal opening to a distal end of the barrel.

9. A hemostasis sealing device comprising:
a housing including a housing wall extending around a passageway;
a first seal portion coupled with the housing, the first seal portion includes a first seal opening extending through the first seal portion;
a second seal portion coupled with the housing, the second seal portion includes a second seal opening extending through the second seal portion and a barrel surrounding a barrel opening in communication with the second seal opening, wherein a barrel wall of the barrel is recessed from the second seal opening within the barrel opening; and
one or more support ribs extending between the barrel and the housing wall, the one or more support ribs each include:
an inner end proximate to the barrel wall,
an outer end having an outer end surface seated against the housing wall, and
wherein the one or more support ribs are configured to transmit compressive forces to the second seal portion from the seating between the outer end surface and the housing wall and the barrel.

10. The device of claim 9 comprising a device enclosure including a device cavity, and the device enclosure includes at least one of the first or second seal portions.

11. The device of claim 9, wherein the first seal portion is coupled with the second seal portion.

12. The device of claim 9, wherein the second seal opening includes a split extending from a distal portion of the second seal portion toward a proximal portion of the second seal portion.

13. The device of claim 12, wherein the split is offset from the one or more support ribs.

14. The device of claim 9, wherein the second seal opening includes a split extending along the second seal portion from the second seal opening.

15. The device of claim 9, wherein the barrel extends from a distal end of the second seal portion.

16. The device of claim 15, wherein the barrel opening is aligned with the second seal opening, and the barrel wall of the barrel tapers from near the second seal opening to a distal end of the barrel.

17. A method for hemostasis sealing a guidewire and an instrument comprising:
passing the guidewire through a first seal portion of a hemostasis sealing device configured for reception in a housing;
passing the guidewire through a second seal portion of the hemostasis sealing device;
sealing the second seal portion around the guidewire, sealing around the guidewire includes:
compressively engaging an outer end surface of at least one support rib with a housing inner surface;
transmitting compressive forces from the engaged outer end surface through the at least one support rib to a barrel surrounding a second seal opening of the second seal portion, and a barrel wall of the barrel is spaced from the second seal opening within the barrel; and
biasing the second seal portion into sealing engagement around the guidewire with the transmitted compressive forces through the barrel;
passing the instrument through the first seal portion and the second seal portion; and
sealing the first seal portion around the instrument.

18. The method of claim 17 comprising sealing the second seal portion around the instrument, sealing around the instrument includes:
engaging the outer end surface of at least one support rib with the housing inner surface,
transmitting compressive forces from the engaged outer end through the at least one support rib to the second seal portion, and
biasing the second seal portion into sealing engagement around the instrument with the transmitted compressive forces.

19. The method of claim 17, wherein the second sealing portion includes a split extending from a distal end of the second sealing portion toward a proximal end of the second sealing portion, and biasing the second seal portion into sealing engagement includes biasing opposed sides of the split together.

20. The method of claim 17, wherein the barrel extends distally from the second seal portion, and
comprising bracing the second seal portion against misalignment or inversion with the barrel.

* * * * *